United States Patent [19]
Vaught et al.

[11] Patent Number: 5,264,912
[45] Date of Patent: Nov. 23, 1993

[54] SPECKLE REDUCTION TRACK FILTER APPARATUS FOR OPTICAL INSPECTION OF PATTERNED SUBSTRATES

[75] Inventors: John L. Vaught, Palo Alto; Michael E. Fein, Moutain View; Armand P. Neukermans, Palo Alto, all of Calif.

[73] Assignee: Tencor Instruments, Mountain View, Calif.

[21] Appl. No.: 832,379

[22] Filed: Feb. 7, 1992

[51] Int. Cl.$^5$ .................. G01N 21/88; G02B 27/46
[52] U.S. Cl. ...................... 356/237; 250/550; 356/71; 359/559
[58] Field of Search .......... 356/71, 237; 250/550; 359/559, 564

[56] References Cited

U.S. PATENT DOCUMENTS

| | | | |
|---|---|---|---|
| 3,658,420 | 4/1972 | Axelrod | 356/71 |
| 3,729,252 | 4/1973 | Nelson | 359/559 X |
| 3,790,280 | 2/1974 | Heinz et al. | 356/71 |
| 3,972,616 | 8/1976 | Minami et al. | 356/71 |
| 3,981,562 | 9/1976 | Anthon | 356/71 X |
| 4,806,774 | 2/1989 | Lin et al. | 250/550 |
| 4,895,446 | 1/1990 | Maldari et al. | 356/336 |
| 5,172,000 | 12/1992 | Scheff et al. | 250/550 |
| 5,177,559 | 1/1993 | Batchelder et al. | 356/237 |

OTHER PUBLICATIONS

Thomas, C. E., Applied Optics, vol. 7, No. 3, p. 517 ff. (Mar. 1968).
George, Nicholas et al., Applied Optics, vol. 6, pp. 1202 ff. (Jun. 1973).

Primary Examiner—Vincent P. McGraw
Attorney, Agent, or Firm—Schneck & McHugh

[57] ABSTRACT

An apparatus used to inspect patterned wafers and other substrates with periodic features for the presence of particles, defects and other aperiodic features in which a spatial filter placed in the Fourier plane is used in combination with either broadband illumination, angularly diverse illumination or both. In contrast to prior devices that direct light from a single monochromatic source through a pinhole aperture stop, embodiments are describes that illuminate a patterned substrate using (1) a single monochromatic source with a slit-shaped aperture stop for angularly diverse illumination, (2) a single broadband source with a pinhole aperture stop for broadband illumination, (3) a single broadband source with a slit-shaped aperture stop for both broadband and angularly diverse illumination, or (4) multiple sources with an aperture stop for each source for at least angularly diverse illumination. The spatial filters for these illumination systems are characterized by opaque tracks in an otherwise transmissive filter for blocking the elongated bands produced by diffraction from the periodic features on the illuminates substrate. The filter may be made photographically by exposing high contrast film placed in or near the Fourier plane to the diffracted light from a defect and particle frame substrate having only periodic features. Light scattered from the aperiodic features is able to substantially pass through the filter and be imaged onto, a CCD array, vidicon camera or TDI sensor.

39 Claims, 6 Drawing Sheets

SPECKLE REDUCTION TRACK FILTER APPARATUS FOR OPTICAL INSPECTION OF PATTERNED SUBSTRATES

TECHNICAL FIELD

The invention relates to optical detection of microscopic contaminants on light diffracting substrates, particularly on patterned semiconductor wafers.

BACKGROUND ART

In the field of contaminant detection on semiconductor wafers there is a class of instruments for inspection of bare or unpatterned wafers. These instruments use light scattering from a scanning laser beam into single-element or multiple-element light collectors to detect the presence of particles on a bare wafer. In one such device where the position of the beam is known, as well as the amount of light scattering from the particles or defects in adjacent scans, a picture of the light scattering particles is inferred.

Once a wafer is patterned, the simple light scattering approach for the detection of contaminants becomes more difficult. If the wafer has topological features, which are inherent in the fabrication of circuits on wafers, there is so much scattering from noncontaminant features that any scattering signal from contaminants is usually lost. Some approaches of the prior art use redundancy or periodicity in the patterns to separate the unwanted scattering signal from the desired signal.

Redundancy in circuit patterns is used in integrated circuit defect and contamination imaging in U.S. Pat. No. 4,806,774 to L. Lin et al. Here, an inspection system employs a Fourier transform lens and an inverse Fourier transform lens positioned along an optic axis to produce from an illuminated area of a patterned specimen wafer a spatial frequency spectrum whose frequency components can be selectively filtered to produce an image pattern of defects in the illuminated area of the wafer. The filtered image strikes the surface of a two-dimensional photodetector array which detects the presence of light corresponding to defects in only the illuminated on-axis wafer die.

In U.S. Pat. No. 4,895,446, particularly in FIG. 3, Maldari et al. disclose use of a mask to filter light diffracted from a patterned wafer. A lens above the wafer forms a Fourier transform of the surface on the mask. The mask contains a pattern corresponding to the Fourier transform of the patterned surface. All light, except that scattered from particles is blocked by the mask. A lens images this light onto a camera.

U.S. Pat. No. 3,972,616, to Minami et al., discloses the use of a spatial filter in combination with two light sources, one of which is a laser and the other of which is a broadband incoherent source. This system produces two superimposed images; a laser-light image from which the spatial filter has removed most information except bright spots at the locations of defects, and an incoherent-light image which shows the shape of the complete pattern being inspected, so that the location of the defects can be identified. In order for the incoherent-light image to fulfill its function, it is necessary that the spatial filter not block most of the information in this image.

From these examples it will be seen that others have previously recognized the value of spatial filtering in detecting particles and defects in patterned wafers with redundant circuit features. The advantage of using the spatial filter is that it reduces the amount of information that the computer must sift through in order to identify defects. A disadvantage of the spatial filter is that it has generally been thought to require the use of a monochromatic and collimated illumination source, usually a laser source, which in turn makes the system vulnerable to speckle noise. A further disadvantage of monochromatic illumination is that resonance effects cause monochromatic particle-detection systems to be relatively insensitive to particles of certain sizes related to the wavelength of illumination.

It is well known that when a laser, or other source having substantial spatial and temporal coherence, is used to illuminate a surface whose patterning or roughness has a depth on the order of a wavelength or more, and in which the patterning or roughness has significant components at a lateral spatial frequency smaller than the optical resolution of the viewing optics, then the image will include a random mottling of the surface, called speckle, which is very difficult to distinguish from features of interest, such as particles of dirt.

Speckle is caused by the coherent summation, i.e. interference, of the reflected light from different high and low areas of the rough surface, all of which lie within one optically-resolvable sub-area of the surface. The presence of speckle raises substantially the minimum size of defect or particle that can be detected. Speckle can be reduced or eliminated by a variety of known methods, two of which are to make the illumination spectrally diverse and to make the illumination angularly diverse.

It has not seemed possible until now to build an inspection machine which applies a spatial filter effectively to light from a broadband light source, because the broadband light source would cause the information in the Fourier plane to spread out, making it seemingly impossible to construct a useful spatial filter (the fact that an ordinary spatial filter is ineffective for polychromatic light is in fact the basis of operation of the device in U.S. Pat. No. 3,972,616, cited above). There have been devices combining spatial filters with angularly diverse light sources, but they have typically employed complex moving mechanisms to overcome the smearing of the Fourier-plane image by the angular diversity. In one such device, the spatial filter is rotated in the Fourier plane, in synchronism with the rotation of a collimated light source, so that the position of the dark spots on the filter tracks the position of the diffracted spots from the pattern being inspected. An early description of such a device appears in C. E. Thomas, *Applied Optics*. vol. 7, no. 3, p. 517 ff. (March 1968).

An object of the invention was to devise an inspection apparatus for patterned wafers with redundant features employing a spatial filter but with anti-speckle characteristics.

SUMMARY OF THE INVENTION

The above object has been achieved by devising a new kind of spatial filter which is used in the Fourier plane of a patterned wafer inspection apparatus. The filter is used in combination with either broadband illumination, angularly diverse illumination or both.

As in the prior art, the present invention is used to inspect substrates having periodic features, such as patterned semiconductor wafers of the type that diffract light from redundant features within die patterns. It is the overall die patterns which cause diffraction.

Sources used in the present invention have one or more beams which are focused onto the periodic features, through an optical system having a pinhole aperture stop, to produce, by diffraction, a plurality of spectral lines found in a plurality of spectral dispersion orders, with each order forming an elongated band. These elongated bands are blocked by opaque tracks on an otherwise transmissive filter. The light which is able to pass through the filter is light coming from defects or particles on the substrate.

In order to obtain sufficient light intensity from a non-laser light source, the source can be an extended source, having a substantial angular extent around a particular central direction. In this case, the pinhole aperture is extended to a rectangular, elongated slit. The slit-shaped aperture causes the Fourier plane image to spread to the elongated band shaped image described above. As an alternative to an extended source, a plurality of different sources may be used with angular diversity among sources. All such sources generate beams which pass through an aperture and the sources may have the same or different wavelengths. The resulting diffraction pattern is a band shaped image of the kind described above.

It should be noted that the use of a slit-shaped aperture stop has several advantages. When the illumination source lacks the extraordinary brightness of a laser, extending the shape of the aperture from pinhole to slit permits the use of much more light from the source; this can be crucial in attaining useful operating speed in a practical inspection instrument. Also, even when the source is a laser that is inherently capable of sending very high optical power through a pinhole aperture, the provision of angular diversity (coupled with known means of reducing the spatial coherence of light coming through different parts of the aperture), can help to reduce speckle.

If the light source employed is itself of low spatial coherence, no special means are likely to be needed to achieve spatially incoherent illumination of the slit aperture. With a source of high spatial coherence, one well-known means of reducing spatial coherence would be a rotating ground-glass plate placed in the optical path between the light source and the slit. The thickness perturbations in the plate would introduce a random phase relationship among different portions of the slit. The plate would need to rotate fast enough so that the phase relationships would change by amounts on the order of 360° during the time when one pixel of data was being collected. Because means for reducing spatial coherence are well known, no further details of such methods will be given here.

The filter of the present invention may be manufactured by placing photographic film in the Fourier plane and recording the bands with a sufficient exposure that adequate opacity will result when a negative image is developed. This negative image may serve as a filter or as a master to produce similar filters. The filter will have a plurality of opaque tracks, corresponding to the bands mentioned above, in a transmissive field.

Light which passes though the filter corresponds to non-periodic features such as particles and substrate defects. This light is directed onto a two-dimensional linear array or a camera. The wafer or beam may be moved to inspect various areas of a substrate.

BEST MODE FOR CARRYING OUT THE INVENTION

Figure 1:
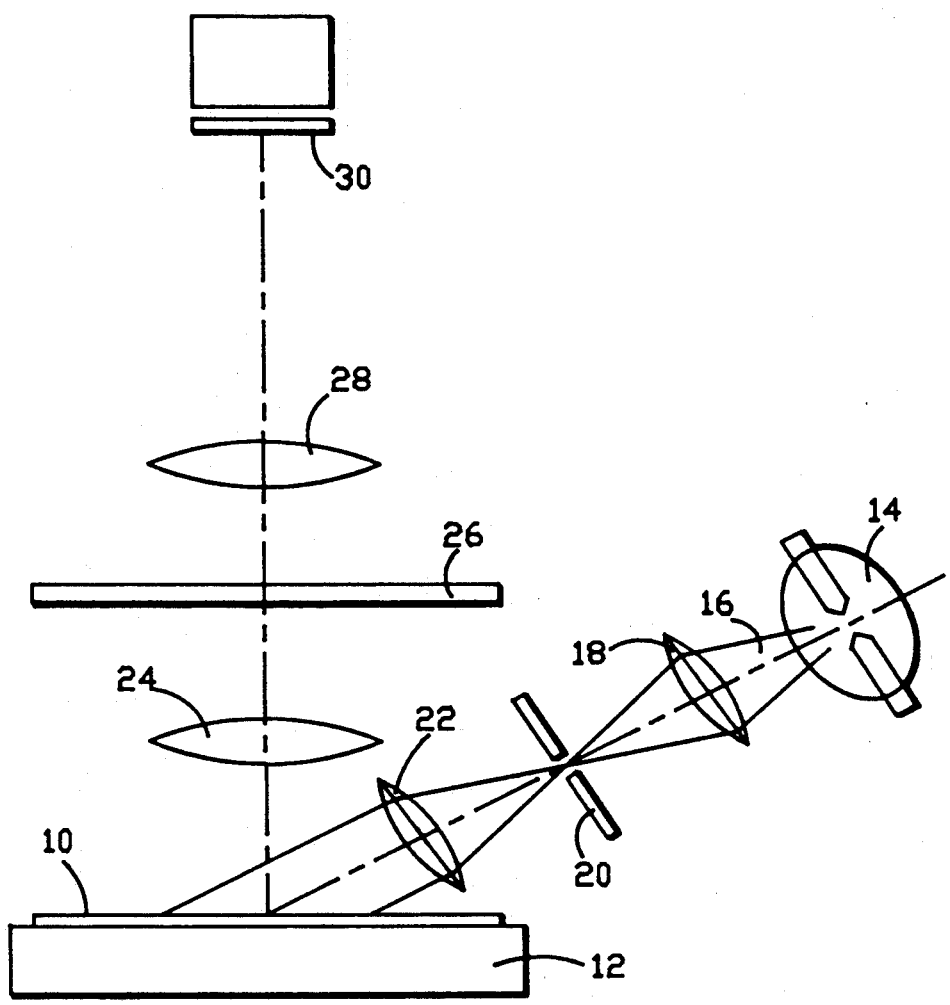
FIG. 1 is an elevation view of a first embodiment of an optical inspection system in accord with the present invention.

With reference to FIG. 1, a patterned wafer 10 is shown to be supported by a wafer chuck 12. The patterned wafer contains a plurality of integrated circuit die separated by perpendicular streets. Each die is an integrated circuit chip. The dies have topographic features, such as mazes separated by valleys in accord with circuit patterns laid out on each die. It is commonplace that wires or metallization which form part of the circuit patterns often run in the same direction, appearing as parallel lines or rulings when viewed in a microscope. A memory chip may have many thousands, or perhaps a million or more transistors, all formed by line patterns on the chip. The spacing between lines on a single chip or the spacing between lines on adjacent chips or between streets separating adjacent chips gives rise to diffraction patterns of a beam of light illuminating a wafer. Wafers may be designed so that line patterns promote strong diffraction, such as by running lines parallel to each other while maintaining a uniform spacing between lines wherever possible. Wafers not optimized in this manner will still diffract light from streets and other regular features, but not as strongly. A wafer having the capability of diffracting light is the patterned wafer 10.

An arc source 14, such as a mercury, xenon, or carbon arc lamp forms a broadband source of beam 16. A focusing lens 18 directs the beam through a pinhole aperture stop 20 where the beam is limited to the extent that only a narrow angular range of rays are present in the light striking the patterned wafer 10. This light is delivered onto the wafer by collimating lens 22.

Light impinging upon closely spaced, light diffracting features on wafer 10 will be directed in various directions, corresponding to several diffraction orders. Some of these orders are gathered by an objective lens 24 and focused upon a spatial filter 26 disposed in the Fourier plane. As explained below, light from the periodic features is filtered by the spatial filter 26, while light from defects is transmitted through the filter and to inverse transform lens 28 which directs light onto the image plane of a two-dimensional imaging device 30, which may, for example, be a CCD video camera. If the periodic features have been filtered by the spatial filter 26, only particles and defects will pass to the imaging device 30. The filter theory may be understood as follows.

Assume for a moment that the beam 16 has also been filtered spectrally so as to provide light of only a narrow wavelength range. This is actually not the case, but the filter assumption is for ease of understanding the invention. If a fine periodic pattern is present on wafer 10, there will typically be several discrete spots of light in the Fourier plane, each spot corresponding to a different diffraction order (i.e. a different angle at which light is diffracted by the periodic pattern). If, now, we imagine the wavelength of the spectral filter to gradually be changed, each spot will move, monotonically with wavelength, because diffraction angles are typically given by a formula such as:

$$\sin(\Theta) = m \frac{\lambda}{d} - \sin(i)$$

where i is the angle of incidence, m is the order of diffraction, d is the spacing of the grating causing the diffraction, and $\sin(\Theta)$ is the sine of the angle of the diffracted rays leaving the surface, and $\lambda$ is the wavelength.

The above formula, taken from Jenkins and White, *Fundamentals of Optics*, 4th ed., p. 360, applies to diffraction by a one-dimensional grating, but similar formulae apply to diffraction by complicated two-dimensional periodic structures. The sine of the angle of diffraction always changes in proportion to wavelength. Rays leaving the wafer 10 at a particular angle come to a focus at a corresponding location in the Fourier plane, so that as angle $\theta$ changes, the Fourier-plane spot moves. If the imaginary spectral filter is varied with respect to wavelength over the full spectral range that we intend to use when the inspection device operates then each spot traces out a straight or curvilinear track in the Fourier plane. If we remove the spectral filter and let all wavelengths be present simultaneously, then each former spot will appear as a band.

It may be said, as a generalization, that speckle reduction becomes more effective as the spectral bandwidth of the source is increased, and that any amount of bandwidth increase that can be achieved is desirable. A useful practical target is at least about a ratio of 1.5 in extreme wavelengths, such as the range from 400 nm to 600 nm wavelength. With such a range, a height difference between two points on the substrate which measures 0.5 wavelengths deep at the long extreme wavelength will measure 0.75 wavelengths deep at the short extreme. Interference will be constructive at the long extreme and destructive at the short extreme. This will assist in suppressing speckle.

It is difficult to obtain enough light intensity from a non-laser source when there is a pinhole aperture 20 in the system. We improve upon the basic invention by permitting the illuminator to have substantial angular extent in a particular direction. The pinhole aperture 20 is preferably extended into a slit. The slit-shaped aperture stop causes each Fourier-plane spot to spread into a strip, just as did the use of multiple colors. By orienting the slit so as to spread out the light in substantially the same direction as did the spectral dispersion bands, it is still possible to make a spatial filter, comprised of multiple dark or opaque stripes on a clear or transmissive field, which blocks most of the light diffracted by the periodic pattern, while passing a significant fraction of the light scattered by particles. It will be understood by those skilled in the art of optical design that, in order to make the slit-shaped aperture stop effective, lens 18 must be evolved, perhaps into a multi-lens system, so as to ensure that the slit is filled with light from source 14. Methods of designing such a lens or lens system are well known.

In FIG. 1, the illumination delivered to wafer 10 has spectral diversity, because arc source 14 emits light over a range of different wavelengths, thereby forming a broadband source. The illumination also has an amount of angular diversity inasmuch as the angular range of light striking wafer 10 is controlled by aperture stop 20, which has been evolved from a pinhole to a slit having substantial extent in one direction. This angular diversity contributes to speckle reduction as previously described.

It is possible to achieve spectral diversity not only by using a source such as an arc lamp, which has a generally-continuous broad spectral output, but alternatively by using a source that emits several discrete spectral lines over a substantial spectral interval, or by combining light from a plurality of separate single-line sources. For example, Nicholas George and Atul Jain described, in Applied Optics, vol. 6, pp. 1202 ff. (June 1973), the use of a multiple-line argon laser to reduce speckle. In that same article, the authors reported the simulation of speckle reduction by the use of six different laser lines spread over a total spectral bandwidth of 150 nm. Their work was a simulation, rather than a direct demonstration, in that they produced the six well-separated spectral lines by filtering light from an arc lamp, rather than by using real lasers.

Figure 2:
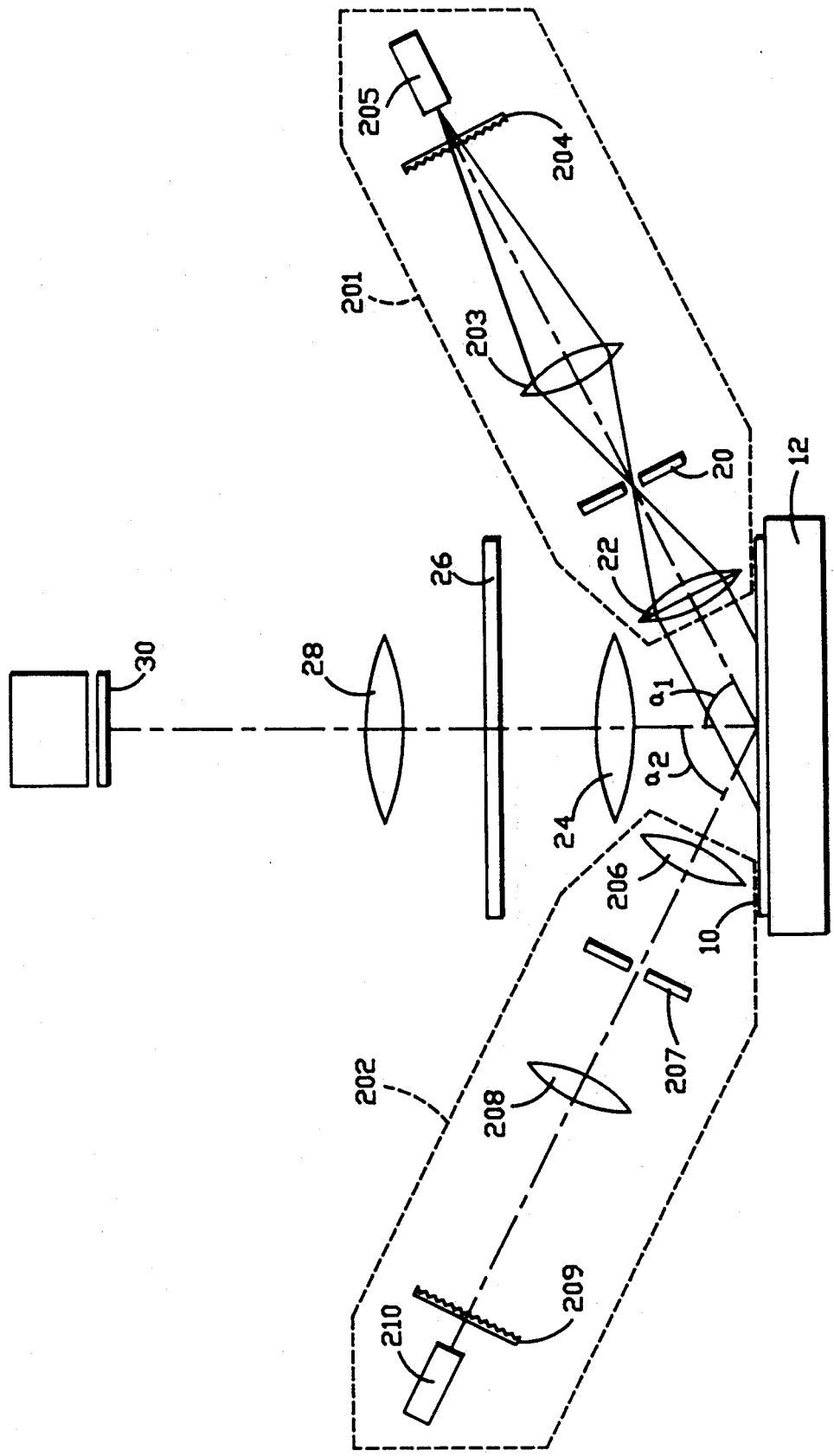
FIG. 2 is an elevation view of a second embodiment of an optical inspection system in accord with the present invention.

FIG. 2 shows that angular diversity of the illumination source may be carried further. This figure also gives an example of one way in which a laser source may be used to produce light having substantial angular diversity. Two separate illumination channels have been provided. A first illumination channel 201 includes a laser 205, diffuser 204, lens 203, aperture stop 20 and collimating lens 22. A second substantially similar illuminator 202 includes a laser 210, diffuser 209, lens 208, aperture stop 207, and collimating lens 206. Light from both illuminators impinges upon wafer 10, supported on wafer chuck 12. Light from the patterned wafer is diffracted toward the spatial filter 26 after passing through objective 24. Once again, light originating from defects or scattered from particles on the wafer will pass through the spatial filter 26 and be collected by lens 28 where the light is then delivered to the imaging device 30 as a focused image. Light from illuminator 201 is generally disposed about elevation angle $a_1$. Light from illuminator 202 is generally disposed about angle $a_2$, which may be different from angle $a_1$. The two illuminators are shown, for convenience in illustration, as arriving from azimuth angles that are 180° apart, but in general they may arrive from any two azimuth angles, and may in fact have the same azimuth angle but different elevation angles. Typical elevation angles may be between 50° and 80° from normal incidence.

Diffuser 204 has the purpose of increasing the angular diversity of light emitted by laser 205, so that this light can be imaged by lens 203 to fill aperture stop 20. In the absence of the diffuser, the effect of the excellent collimation of light emitted by laser 205 might be that stop 20 would not be fully illuminated. Diffuser 209 has a function similar to that of diffuser 204.

Each of the two illuminators will create a separate pattern of light in the Fourier transform plane created by lens 24. By photographic or other means we may generate a spatial filter 26 to be placed in the Fourier plane of the objective. Spatial filter 26 blocks most of the pattern-diffracted light originating in either illuminator, while still transmitting a useful fraction of the light scattered by nonperiodic features on wafer 10, such as particles or pattern defects. The portion of the area of filter 26 which must be opaque may be nearly twice as large as the opaque area required with a single source, but this is acceptable as long as enough open area remains to transmit a useful fraction of light scattered by non-periodic features. The open area should preferably be more than about 50% of the total area of the filter.

The angular separation between the first and second illuminators 201 and 202 gives greater angular diversity, for the purpose of speckle reduction, than could be easily achieved with a single illuminator. The two lasers may have the same or different wavelengths, but different wavelengths provide some spectral diversity. Aperture stop 20 is again preferably a rectangular slit to increase the amount of illumination through the aperture while also increasing angular diversity of illumination.

Figure 3:
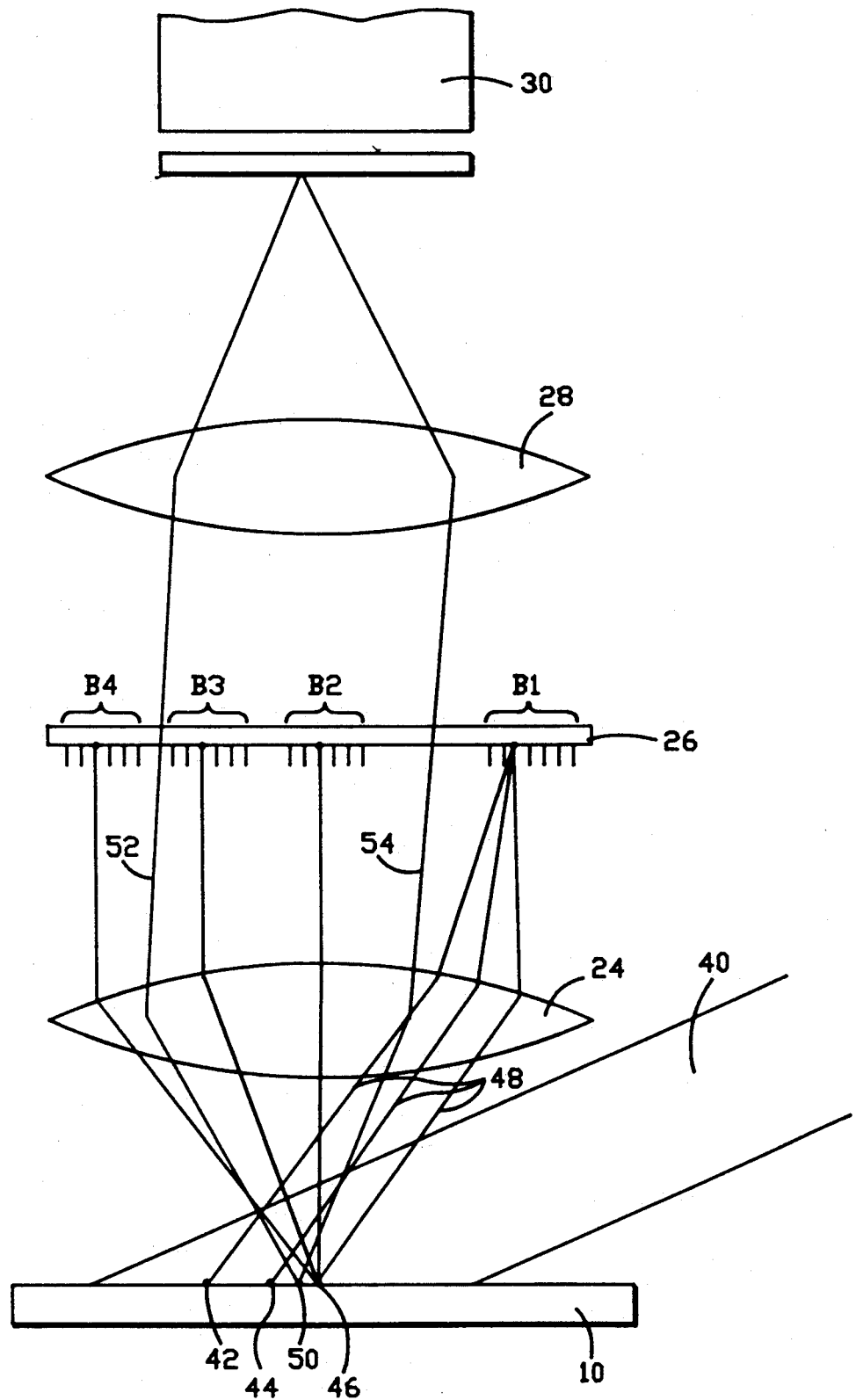
FIG. 3 is a detail illustrating diffraction from a test surface using the apparatus of FIG. 1.

In FIG. 3, the collimated illuminating beam 40 is shown impinging on wafer 10 at a relatively shallow angle. A number of redundant features 42, 44 and 46, like protrusions, are seen to project above the wafer. These wafer features are similar to the troughs and ridges of gratings in their ability to diffract light. Such diffracted light is illustrated by rays 48 which are focused by the objective lens 24 to the filter 26. Various wavelengths or angular components form a band B1 which is generally rectangular in character. Other diffraction orders yield the bands B2, B3 and B4, all lying in the Fourier plane. As previously mentioned, photographic film is placed in the Fourier plane then exposed and developed. The exposure or the development or both are such that the various bands of light are darkened or made opaque. This forms tracks in a clear or optically transmissive field. In FIG. 3, a particle 50 is shown scattering rays of light 52 and 54. This light passes through the spatial filter 26 and then impinges upon lens 28 where the rays are refracted toward the imaging device 30. The rays 52 and 54 pass between opaque tracks in filter 26 most of the time. The area of the filter blocked by opaque tracks is preferably less than one-half and usually on the order of 20 percent in a preferred filter configuration. Imaging device 30 may be a CCD array (which may, for example, have 768 pixels horizontally and 494 pixels vertically) or a vidicon camera. Many other forms of sensors, such as the high-speed multiple-output time-delay-integration (TDI) sensor are also usable with this invention. Wafer chuck 12, which carries wafer 10, is movable in an x-y plane so that various areas of the wafer can be viewed. Each pattern viewed may be stored in a memory so that a composite view of an entire wafer may be had.

Figure 4:
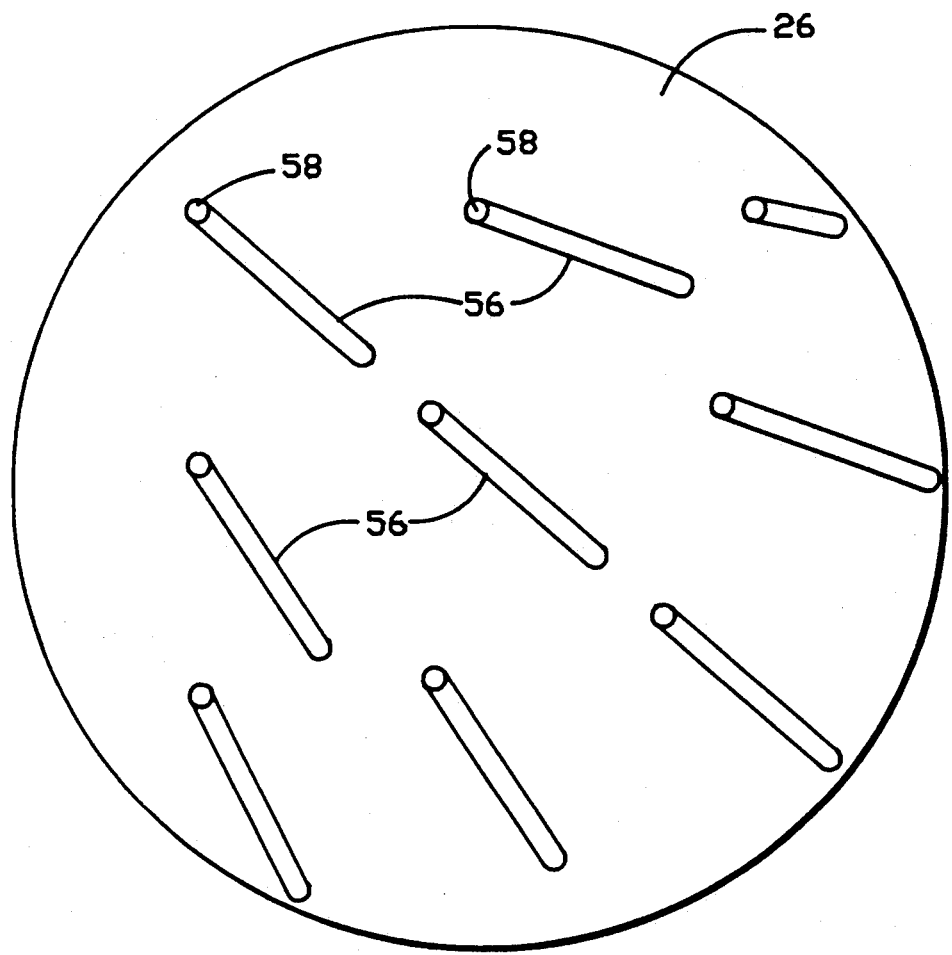
FIG. 4 is a top plan view of a spatial filter in accord with the present invention for use with the apparatus of FIG. 1.

In FIG. 4, the spatial filter 26 is shown having opaque tracks 56. The dot 58 at the head of each track represents the shortest wavelength from the source and one end of slit-like aperture stop 20. If the aperture stop were a pinhole, and if only this one wavelength were present, the pattern on the filter would be a plurality of spots. However, this is the filter design of the prior art which does not compensate for speckle. In the present invention, speckle is reduced with spectral and/or angular diversity from the source or sources by forming the plurality of tracks on spatial filter 26. The locations of spots 58 are related to the period of the redundant features on the wafer. The filter may either be the photographic negative previously described or a copy. High quality negatives and copies may be made by exposing and developing high resolution photoplates of the type used in the semiconductor industry, or by using high-contrast line art film, such as Kodak Technical Pan film.

It will often be desirable to modify the spatial filter by making the size of the opaque regions somewhat larger than the regions where light diffracted by patterns strikes, so that the filter will work effectively even in the presence of slight imperfections in alignment. One method of doing this is to record the filter photographically, with the film at an axial location slightly away from the Fourier plane. The resultant defocusing will slightly enlarge the dark sports, and if a high-contrast film is used, the enlarged spots will be opaque right up to their edges. A property-made spatial filter will have stripes wide enough to ensure blocking most of the pattern-diffracted light from a substrate, even in the presence of typical amounts of alignment error, but not so wide as to block more than about 50% of the total optical aperture of the viewing system.

The spatial filter shown in FIG. 4 has an appearance typical of that which one would see if the elevation angle of the illuminating beam were about 45° from vertical, and the azimuth of the illuminating beam were about 45° to the streets and avenues of a patterned wafer having generally rectilinear ("Manhattan") geometry. It should be emphasized that the method of this invention can be employed with the illumination at this or any other angular orientation with respect to the wafer geometry. Both elevation and azimuth angles may be varied.

Figure 5:
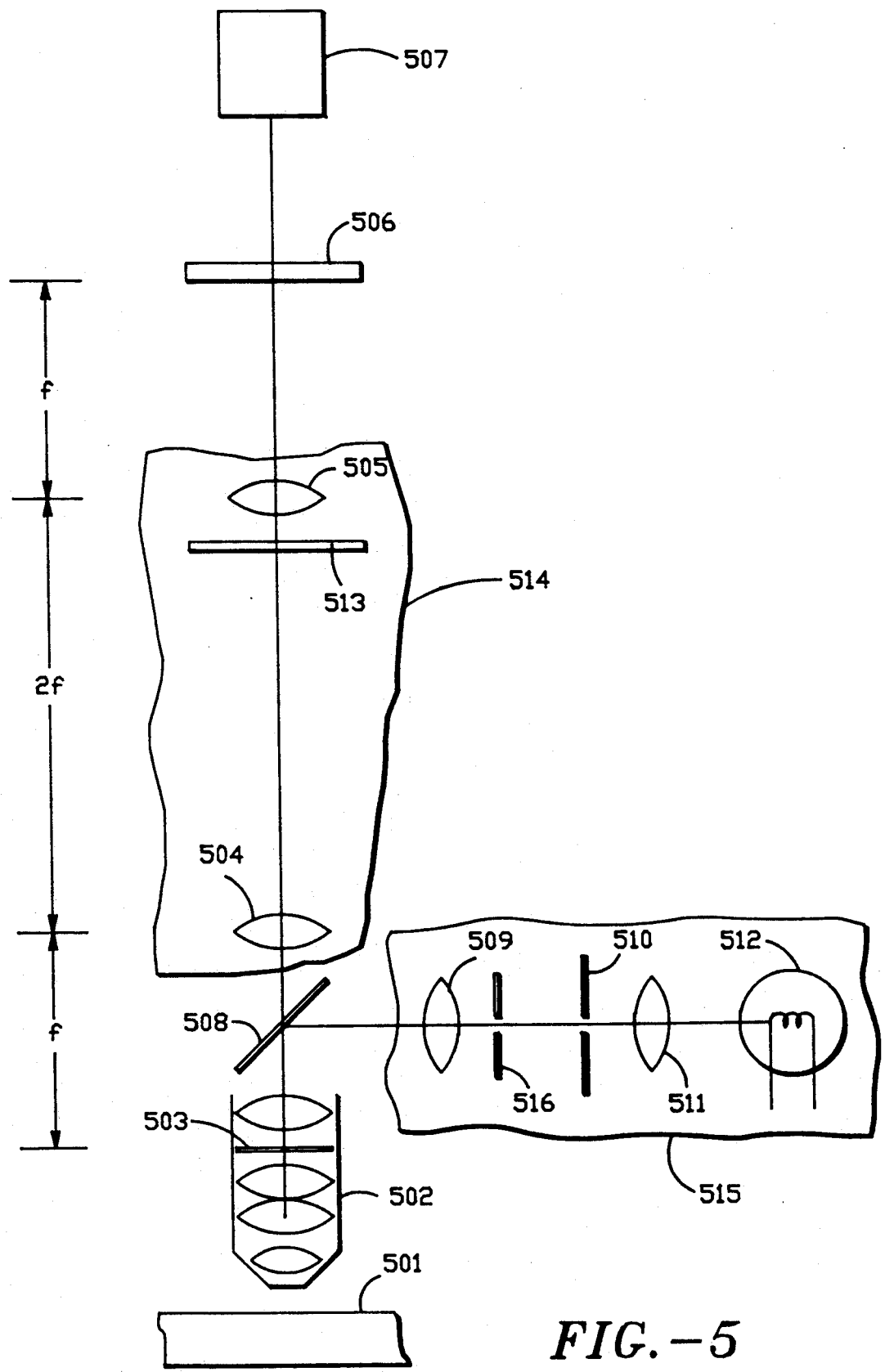
FIG. 5 is an elevation view of an alternate embodiment of an optical inspection system in accord with the present invention, in which illumination is supplied through the viewing objective lens.

FIG. 5 illustrates an embodiment of our invention in which the illumination is normal to the wafer. This figure also illustrates one of the many alternative optical systems which may be used to employ our inventive spatial filter design. Wafer 501 is viewed by multi-element microscope objective 502. This microscope objective, like many of those available on the market, has its Fourier plane 503 at an internal level in the objective, where it is not accessible for placement of a spatial filter. Lenses 504 and 505 constitute relay lens system 514, which produces an image of Fourier plane 503 at the location of spatial filter 506. In this simple example, it is assumed that each of lenses 504 and 505 has focal length f. They are spaced, as shown in the figure, so as to constitute an afocal relay system with magnification of 1. This particular arrangement is not necessary to the invention. What is necessary is that by some means either the Fourier plane or its image be made accessible for placement of a spatial filter.

In the absence of relay system 514, the objective would form an image of the wafer surface at plane 513. The effect of the relay is to re-form this image at the entrance face of image detector 507.

Illumination in this system is provided by way of beamsplitter 508. Illuminator 515 comprises lenses 509 and 511, light source 512 (which may be for example an incandescent lamp, an arc lamp, or a multiline laser), field stop 516 and aperture stop 510. It will be most useful for aperture stop 510 to be a pinhole. The effect of this illuminator arrangement is to deliver illumination that is generally normal to the wafer.

Figure 6:
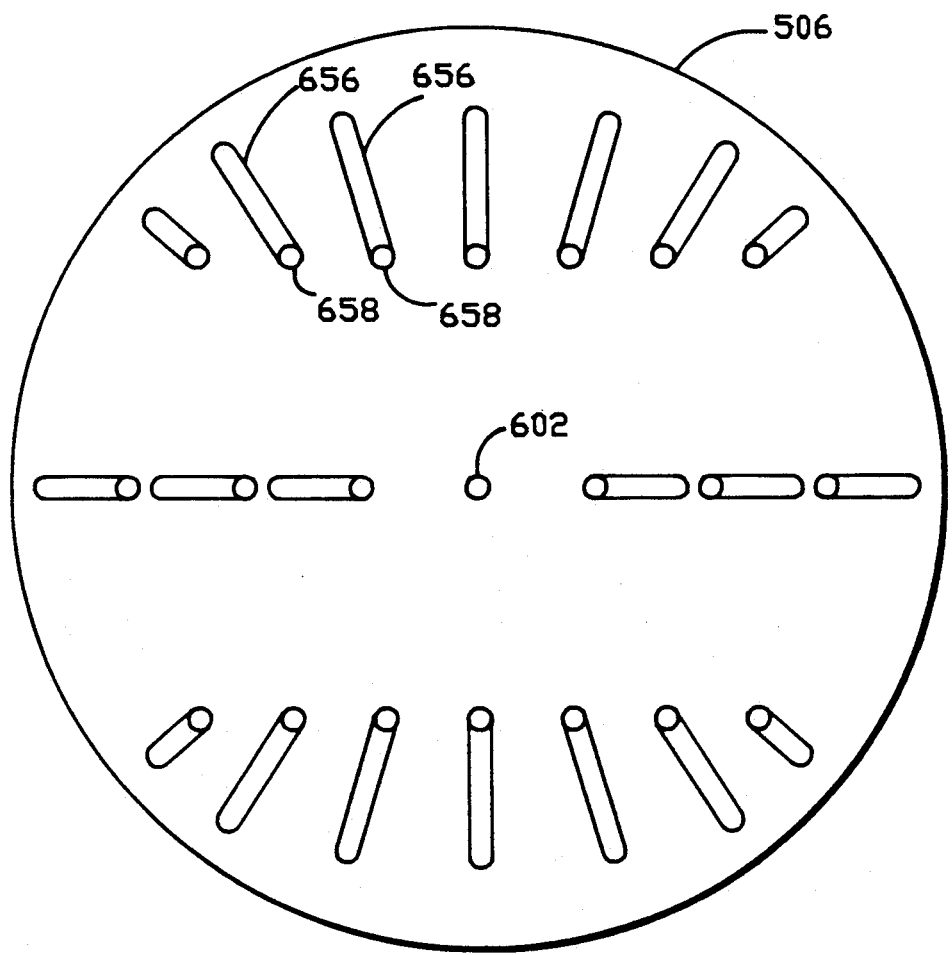
FIG. 6 is a plan view of a spatial filter in accord with the present invention for use with the apparatus of FIG. 5.

FIG. 6 shows a spatial filter 506 that would be useful in the apparatus of FIG. 5. The filter has radially-oriented opaque tracks 656, in a generally transmissive field. The dots at the head of each track represent the shortest wavelength provided by source 512. Opaque spot 602 represents the location where objective 502 will focus light that is specularly reflected from the wafer. This light (which is sometimes referred to as "zero-order diffraction") must be blocked, in the same way that tracks 656 block the other diffracted orders of light.

A point illustrated by the system of FIG. 5 is that it is not necessary to have separate lenses to form the Fourier transform and the final image. In the example of FIG. 1, which would be typical of a system using an infinity-corrected objective lens, the transform was formed by lens 24 and the final image by lens 28. In the system of FIG. 5, which is typical of a system using a finite-tube-length microscope objective, both the Fourier transform and the image are formed (at planes 503 and 513 respectively) by objective lens 502. What is essential to the practice of our invention is that there be one or more lenses so disposed as to produce an accessible Fourier plane and an accessible image plane. Many different arrangements for accomplishing this purpose are known to those skilled in optical system design.

It is characteristic of spatial filters made in accordance with our invention that the opaque stripes appear approximately as segments of straight lines or curves radiating from an imaginary point, which may be within or outside of the area of the filter itself. For example, in FIG. 6, that point is at the center of the filter. In FIG. 4, the point is above and to the left of the filter. This phenomenon may be understood by recognizing that, as is well known, each point in the Fourier plane represents a particular angle at which light is diffracted from the substrate being inspected. The apparent center from which the stripes seem to radiate corresponds to the angle at which the specularly-reflected beam leaves the substrate.

A potentially useful variation of our invention may be described by returning to the simple apparatus of FIG. 1, with a broadband light source and a pinhole aperture. Spatial filter 26 may have the general appearance of FIG. 4. Because aperture stop 20 is a pinhole, each diffraction order in the Fourier plane will be a simple dispersed spectrum, with short-wave light at one end of the spectrum and long-wave light at the other. It may be practical to use dye or thin film technology to construct a variable-wavelength (color) blocking filter instead of a simple opaque stripe, so that each small region of a stripe on the spatial filter will block only the light corresponding to the one particular color which is diffracted to that location by the regular pattern on the substrate being inspected. This will maximize the amount of other light (typically representing defects to be identified) that is able to pass through the spatial filter.

Given present-day technology, the most economical approach by far is to use simple opaque stripes to block all of the pattern-diffracted light. It has proven practical, for many substrates of interest, to construct opaque-stripe filters according to our invention, in which the open area exceeds 50%, so that attenuation of light scattered by small periodic defects does not exceed 50%.

At several points in the above discussion, there has been reference to the Fourier transform of a pattern on a wafer, which has been described as falling in a plane, the "Fourier plane." It is well known that in many real optical systems, the surface in which the Fourier transform lies has curvature. References herein to the Fourier plane should therefore be taken to include two other cases. First, it may be desirable to deal with a curved transform surface by fabricating a spatial filter on a curved substrate which lies close to that surface (this approach will be unusual because of its technical difficulty). The second, and more common way to deal with curvature of the transform surface will be to fabricate the filter on a planar substrate, and locate it close to the true transform surface. By slightly oversizing the opaque areas of the filter, it will be possible to block most light diffracted by periodic patterns, even though the filter is not exactly in the transform surface.

We claim:

1. An inspection device for substrates, such as patterned semiconductor wafers, having periodic features of a type diffracting light into a Fourier plane or surface comprising,
   a broadband source of illumination generating a beam directed along an optical axis at a substrate, the substrate having a repetitive pattern of periodic features, as well as aperiodic contaminants and defects, said periodic features having a spacing diffracting light from said beam in a plurality of spectral lines found in a plurality of spectral dispersion orders, each order of spectral lines forming an elongated band,
   an aperture stop disposed along said optical axis with said beam focused to pass therethrough and onto said periodic features of the substrate,
   a mainly transmissive spatial filter, disposed in the Fourier plane of light diffracted from the substrate, the filter having a plurality of spaced apart opaque tracks blocking said bands of light of the broadband source but transmitting light scattered from said aperiodic features, each track radiating from an imaginary point,
   a two dimensional imaging sensor located a distance from said spatial filter in a position receiving light transmitted through said spatial filter, and
   means for delivering light passing through the spatial filter to said imaging sensor.

2. The apparatus of claim 1 wherein said spatial filter is a Fourier transform filter.

3. The apparatus of claim 2 wherein said Fourier transform filter has been formed photographically with high contrast film placed in a defocused position located slightly away from said Fourier plane, whereby said filter has slightly larger opaque tracks than a perfect Fourier transform filter.

4. The apparatus of claim 1 wherein said spatial filter is a variable-wavelength (color) blocking filter with tracks that are opaque in any given location to that color of light that is diffracted thereto by said periodic features.

5. The apparatus of claim 1 wherein said opaque tracks of said spatial filter radiate outward in position from an apparent center.

6. The apparatus of claim 1 wherein said aperture stop is an elongated slit.

7. The apparatus of claim 1 wherein said aperture stop is a pinhole.

8. The apparatus of claim 1 wherein said optical axis is perpendicular to the substrate, said beam from said source being directed by a beamsplitter along said optical axis for normal incidence upon said substrate.

9. The apparatus of claim 1 wherein said optical axis is oriented at a nonperpendicular elevation angle relative to said substrate.

10. The apparatus of claim 1 further comprising relay optics means for producing an image of said Fourier plane in an image plane accessible to placement of said spatial filter, said spatial filter being disposed in said image plane.

11. The apparatus of claim 1 wherein said imaging sensor is a CCDR array.

12. The apparatus of claim 1 wherein said imaging sensor is a vidicon camera.

13. The apparatus of claim 1 wherein said imaging sensor is a TDI sensor.

14. An inspection device for substrates, such as patterned semiconductor wafers, having periodic features of a type diffracting light into a Fourier plane or surface comprising,
a plurality of sources of illumination generating beams directed at a common region in a substrate, the substrate having a repetitive pattern of periodic features, as well as aperiodic contaminants and defects, said periodic features having a spacing diffracting light from said beams in a plurality of spectral lines found in a plurality of spectral dispersion orders, each order of spectral lines forming an elongated band,
each beam having an aperture stop to control its angular diversity as it impinges on the substrate,
a mainly transmissive spatial filter, disposed in the Fourier plane of light diffracted from the substrate, the filter having a plurality of spaced apart opaque tracks blocking said bands of light of said plurality of sources of illumination but transmitting light scattered from said aperiodic features, each track radiating from an imaginary point,
a two dimensional imaging sensor located a distance from said spatial filter in a position receiving light transmitted through said spatial filter, and
means for delivering light passing through the spatial filter to said imaging sensor.

15. The apparatus of claim 14 wherein said spatial filter is a Fourier transform filter.

16. The apparatus of claim 15 wherein said Fourier transform filter has been formed photographically with high contrast film placed in a defocused position located slightly away from said Fourier plane, whereby said filter has slightly larger opaque tracks than a perfect Fourier transform filter.

17. The apparatus of claim 14 wherein said spatial filter is a variable-wavelength (color) blocking filter with tracks that are opaque in any given location to that color of light that is diffracted thereto by said periodic features.

18. The apparatus of claim 14 wherein said opaque tracks of said spatial filter radiate outward in position from an apparent center.

19. The apparatus of claim 14 wherein said aperture stop is an elongated slit.

20. The apparatus of claim 14 wherein said aperture stop is a pinhole.

21. The apparatus of claim 14 wherein said beams are laser beams.

22. The apparatus of claim 14 wherein said beams have the same wavelength.

23. The apparatus of claim 14 wherein said beams have different wavelengths.

24. The apparatus of claim 14 wherein said plurality of sources is spaced at different elevation angles relative to the substrate between 10° and 40°.

25. The apparatus of claim 14 wherein said imaging sensor is a CCD array.

26. The apparatus of claim 14 wherein said imaging sensor is a vidicon camera.

27. The apparatus of claim 14 wherein said imaging sensor is a TDI sensor.

28. An inspection device for substrates, such as patterned semiconductor wafers, having periodic features of a type diffracting light into a Fourier plane or surface comprising,
a single source of monochromatic illumination generating a beam directed along an optical axis at a substrate, the substrate having a repetitive pattern of periodic features, as well as aperiodic contaminants and defects,
an elongated slit-shaped aperture stop disposed along said optical axis with said beam focused to pass therethrough and onto said periodic features of the substrate, said periodic features having a spacing diffracting light from said beam in a plurality of lines found in a plurality of dispersion orders, each order of lines forming an elongated band,
a mainly transmissive spatial filter, disposed in the Fourier plane of light diffracted from the substrate, the filter having a plurality of spaced apart opaque tracks blocking said bands of light associated with the slit-shaped aperture stop but transmitting light scattered from said aperiodic features, each track radiating from an imaginary point,
a two dimensional imaging sensor located a distance from said spatial filter in a position receiving light transmitted through said spatial filter, and
means for delivering light passing through the spatial filter to said imaging sensor.

29. The apparatus of claim 28 wherein said spatial filter is a Fourier transform filter.

30. The apparatus of claim 29 wherein said Fourier transform filter has been formed photographically with high contrast film placed in a defocused position located slightly away from said Fourier plane, whereby said filter has slightly larger opaque tracks than a perfect Fourier transform filter.

31. The apparatus of claim 28 wherein said opaque tracks of said spatial filter radiate outward in position from an apparent center.

32. The apparatus of claim 28 wherein said optical axis is perpendicular to the substrate, said beam from said source being directed by a beamsplitter along said optical axis for normal incidence upon said substrate.

33. The apparatus of claim 28 wherein said optical axis is oriented at a nonperpendicular elevation angle relative to said substrate.

34. The apparatus of claim 28 further comprising relay optics means for producing an image of said Fourier plane in an image plane accessible to placement of said spatial filter, said spatial filter being disposed in said image plane.

35. The apparatus of claim 28 wherein said imaging sensor is a CCD array.

36. The apparatus of claim 28 wherein said imaging sensor is a vidicon camera.

37. The apparatus of claim 28 wherein said imaging sensor is a TDI sensor.

38. In an inspection system of the type diffracting light in bands of light in a Fourier plane from patterned semiconductor wafers of the type having a plurality of periodic features as well as aperiodic features, such as defects and particles, the improvement comprising, a mainly transmissive spatial filter, disposed in the Fourier plane of light diffracted from the substrate, the filter having a plurality of spaced apart opaque tracks opaque tracks blocking said bands of light but transmitting light scattered from said aperiodic features, each track radiating from an imaginary point.

39. The apparatus of claim 38 wherein said spatial filter is a Fourier transform filter.

* * * * *

UNITED STATES PATENT AND TRADEMARK OFFICE
CERTIFICATE OF CORRECTION

PATENT NO. : 5,264,912
DATED : November 23, 1993
INVENTOR(S) : John L. Vaught et al.

It is certified that error appears in the above-indentified patent and that said Letters Patent is hereby corrected as shown below:

Column 8, line 20, "A property-made spatial filter" should read - - A properly-made spatial filter - -.

Claim 11, column 11, line 12, "CCDR array" should read - - CCD array - -.

Claim 38, column 14, line 1, "tracks opaque tracks" should read - - tracks - -.

Signed and Sealed this

Nineteenth Day of April, 1994

Attest:

BRUCE LEHMAN

Attesting Officer  Commissioner of Patents and Trademarks